United States Patent [19]
Marshall

[11] Patent Number: 5,947,121
[45] Date of Patent: Sep. 7, 1999

[54] TRACHEOTOMY TUBE WATER BLOCKING SYSTEM

[76] Inventor: Patrick Marshall, 1024 Anderson St., New Iberia, La. 70560

[21] Appl. No.: 08/980,470

[22] Filed: Nov. 28, 1997

[51] Int. Cl.$^6$ .......................... A61M 16/00; A62B 9/02; A62B 9/06
[52] U.S. Cl. ................ 128/207.15; 128/207.16; 128/912
[58] Field of Search ................ 128/207.14, 207.15, 128/207.16, 200.26, 911, 912, DIG. 26

[56] References Cited

U.S. PATENT DOCUMENTS 4,325,366  4/1982  Tabor ................. 128/207.16
5,616,116  4/1997  Born .................. 128/207.16

Primary Examiner—Kimberly L. Asher

[57] ABSTRACT

A tracheotomy tube water blocking system including a strap adapted for securement around a neck of a wearer. The strap has an aperture through a front portion thereof. The aperture has a cylindrical collar secured therein. The cylindrical collar has an open inner end and an open outer end. The open inner end is dimensioned for coupling with an existing tracheotomy tube of the wearer. An air flow tube is provided having a generally inverted L-shaped configuration. The air flow tube has an upper horizontal portion with an open inner end coupling with the open outer end of the cylindrical collar. The air flow tube includes a lower vertical portion extending downwardly from the upper horizontal portion. The lower vertical portion having an open lower end.

8 Claims, 2 Drawing Sheets

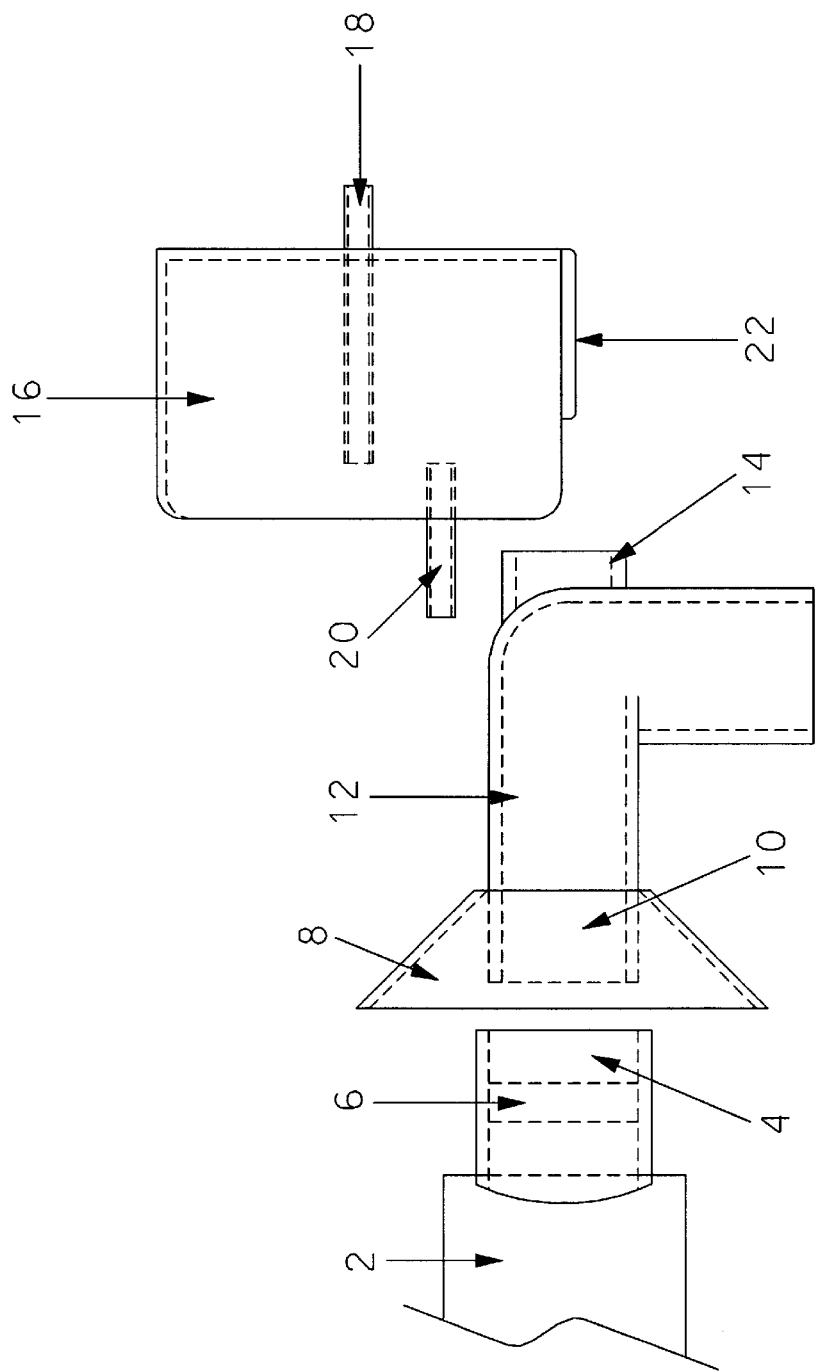

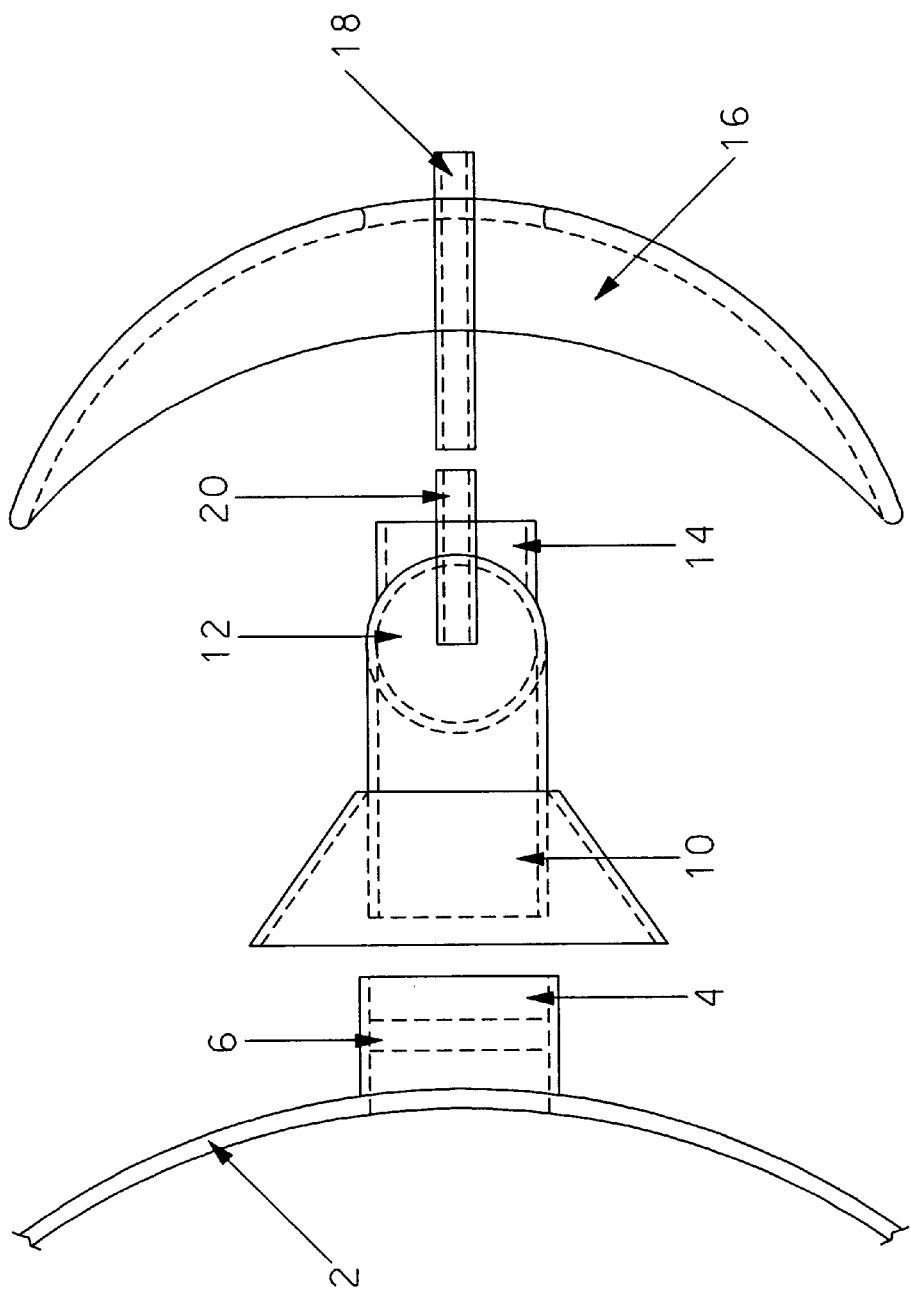

TRACHEOTOMY TUBE WATER BLOCKING SYSTEM

BACKGROUND OF THE INVENTION

1. Field of the Invention

The present invention relates to a tracheotomy tube water blocking system and more particularly pertains to preventing water from entering a trachea tube while showering with a tracheotomy tube water blocking system.

2. Description of the Prior Art

The use of tracheotomy covers is known in the prior art. More specifically, tracheotomy covers heretofore devised and utilized for the purpose of covering an open tracheotomy tube are known to consist basically of familiar, expected and obvious structural configurations, notwithstanding the myriad of designs encompassed by the crowded prior art which have been developed for the fulfillment of countless objectives and requirements.

By way of example, U.S. Pat. No. Des. 309,021 to Beevers; U.S. Pat. No. 4,313,437 to Martin; U.S. Pat. No. 4,325,366 to Tabor; U.S. Pat. No. 4,802,474 to Beevers; U.S. Pat. No. 5,027,811 to Tuxill; and U.S. Pat. No. 5,201,309 to Friberg et al.

While these devices fulfill their respective, particular objective and requirements, the aforementioned patents do not describe a tracheotomy tube water blocking system for preventing water from entering a trachea tube while showering.

In this respect, the tracheotomy tube water blocking system according to the present invention substantially departs from the conventional concepts and designs of the prior art, and in doing so provides an apparatus primarily developed for the purpose of preventing water from entering a trachea tube while showering.

Therefore, it can be appreciated that there exists a continuing need for new and improved tracheotomy tube water blocking system which can be used for preventing water from entering a trachea tube while showering. In this regard, the present invention substantially fulfills this need.

SUMMARY OF THE INVENTION

In the view of the foregoing disadvantages inherent in the known types of tracheotomy covers now present in the prior art, the present invention provides an improved tracheotomy tube water blocking system. As such, the general purpose of the present invention, which will be described subsequently in greater detail, is to provide a new and improved tracheotomy tube water blocking system and method which has all the advantages of the prior art and none of the disadvantages.

To attain this, the present invention essentially comprises an elastic strap adapted for securement around a neck of a wearer. The elastic strap has an aperture through a front portion thereof. The aperture has a cylindrical collar secured therein. The cylindrical collar has an open inner end and an open outer end. The open inner end is positioned inwardly of the elastic strap and the open outer end is positioned outwardly of the elastic strap. The open inner end is dimensioned for coupling with an existing tracheotomy tube of the wearer. The cylindrical collar has an air screen disposed therein. A cover member is provided having a generally frustoconical configuration. The cover member has a wide inner end and a narrow outer end. The wide inner end is positionable over the cylindrical collar. An air flow tube is provided having a generally inverted L-shaped configuration. The air flow tube has an upper horizontal portion with an open inner end extending through the narrow outer end of the cover member for coupling with the open outer end of the cylindrical collar. The air flow tube includes a lower vertical portion extending downwardly from the upper horizontal portion. The lower vertical portion has an open lower end. The air flow tube includes an access port disposed on an upper end of the lower vertical portion. The access port has a lid removably disposed thereon. An arcuate shield portion is adapted for removable securement to the air flow tube. The shield portion includes a central recess dimensioned for receiving the air flow tube therein. The central recess has a receiving sleeve extending inwardly therefrom for mating with a cylindrical pin extending outwardly from the air flow tube.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved tracheotomy tube water blocking system which has all the advantages of the prior art tracheotomy covers and none of the disadvantages.

It is another object of the present invention to provide a new and improved tracheotomy tube water blocking system which may be easily and efficiently manufactured and marketed.

It is a further object of the present invention to provide a new and improved tracheotomy tube water blocking system which is of durable and reliable construction.

An even further object of the present invention is to provide a new and improved tracheotomy tube water blocking system which is susceptible of a low cost of manufacture with regard to both materials and labor, and which accordingly is then susceptible of low prices of sale to the consuming public, thereby making such a tracheotomy tube water blocking system economically available to the buying public.

Even still another object of the present invention is to provide a new and improved tracheotomy tube water blocking system for preventing water from entering a trachea tube while showering.

Lastly, it is an object of the present invention to provide a new and improved tracheotomy tube water blocking system including a strap adapted for securement around a neck of a wearer. The strap has an aperture through a front portion thereof. The aperture has a cylindrical collar secured therein. The cylindrical collar has an open inner end and an open outer end. The open inner end is dimensioned for coupling with an existing tracheotomy tube of the wearer. An air flow tube is provided having a generally inverted L-shaped configuration. The air flow tube has an upper horizontal portion with an open inner end coupling with the open outer end of the cylindrical collar. The air flow tube includes a lower vertical portion extending downwardly from the upper horizontal portion. The lower vertical portion having an open lower end.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a side elevation view of the preferred embodiment of the tracheotomy tube water blocking system constructed in accordance with the principles of the present invention.

FIG. 2 is a plan view of the present invention illustrated in FIG. 1.

The same reference numerals refer to the same parts through the various figures.

DESCRIPTION OF THE PREFERRED EMBODIMENT

With reference now to the drawings, and in particular, to FIGS. 1 and 2 thereof, the preferred embodiment of the new and improved tracheotomy tube water blocking system embodying the principles and concepts of the present invention will be described.

Specifically, it will be noted in the various Figures that the device relates to a tracheotomy tube water blocking system for preventing water from entering a trachea tube while showering. In its broadest context, the device consists of an elastic strap, an air flow tube, a cover member and an arcuate shield portion. Such components are individually configured and correlated with respect to each other so as to attain the desired objective.

The elastic strap 2 is adapted for securement around a neck of a wearer. The elastic strap 2 has an aperture through a front portion thereof. The elastic strap 2 will be provided with opposed free ends with associated adjustable coupling means to secure around the neck of the wearer. The aperture 2 has a cylindrical collar 4 secured therein. The cylindrical collar 4 has an open inner end and an open outer end. The open inner end is positioned inwardly of the elastic strap 2 and the open outer end is positioned outwardly of the elastic strap 2. The open inner end is dimensioned for coupling with an existing tracheotomy tube of the wearer. The cylindrical collar 4 has an air screen 6 disposed therein. The air screen 6 acts as an air purifier to filter out any particulate matter that would otherwise enter into the tracheotomy tube of the wearer.

The cover member 8 has a generally frustoconical configuration. The cover member 8 has a wide inner end and a narrow outer end. The wide inner end is positionable over the cylindrical collar 4. The cover member 8 provides added protection to the coupling of the air flow tube 12 to the cylindrical collar 4 discussed in detail hereafter.

The air flow tube 12 has a generally inverted L-shaped configuration. The air flow tube 12 has an upper horizontal portion 10 with an open inner end extending through the narrow outer end of the cover member 8 for coupling with the open outer end of the cylindrical collar 4. The air flow tube 12 includes a lower vertical portion extending downwardly from the upper horizontal portion. The lower vertical portion has an open lower end. The open lower end serves as an air access opening to allow for the flow of fresh air to the tracheotomy tube of the wearer. The air flow tube 12 includes an access port 14 disposed on an upper end of the lower vertical portion. The access port 14 has a lid removably disposed thereon. The access port 14 provides linear access to the user's tracheotomy tube in the event of an emergency, i.e., the tracheotomy tube is clogged.

The arcuate shield portion 16 is adapted for removable securement to the air flow tube 12. The shield portion 16 includes a central recess dimensioned for receiving the air flow tube 12 therein. The central recess has a receiving sleeve 18 extending inwardly therefrom for mating with a cylindrical pin 20 extending outwardly from the air flow tube 12. The arcuate shield portion 16 provides protection from water directly contacting the other components of the device. The lower edge of the arcuate shield portion 16 is provided with a rubber gasket 22.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modification and changes will readily occur to those skilled in the art, it is not desired to limit the invention to the exact construction and operation shown and described, and accordingly, all suitable modification and equivalents may be resorted to, falling within the scope of the invention.

What is claimed as being new and desired to be protected by Letters Patent of the United States is as follows:

1. A tracheotomy tube water blocking system for preventing water from entering a trachea tube while showering comprising, in combination:

an elastic strap adapted for securement around a neck of a wearer, the elastic strap having an aperture through a front portion thereof, the aperture having a cylindrical collar secured therein, the cylindrical collar having an open inner end and an open outer end, the open inner end being positioned inwardly of the elastic strap and the open outer end being positioned outwardly of the elastic strap, the open inner end dimensioned for coupling with an existing tracheotomy tube of the wearer, the cylindrical collar having an air screen disposed therein;

a cover member having a generally frustoconical configuration, the cover member having a wide inner end and a narrow outer end, the wide inner end positionable over the cylindrical collar;

an air flow tube having a generally inverted L-shaped configuration, the air flow tube having an upper horizontal portion with an open inner end extending through the narrow outer end of the cover member for coupling with the open outer end of the cylindrical collar, the air flow tube including a lower vertical portion extending downwardly from the upper horizontal portion, the lower vertical portion having an open lower end, the air flow tube including an access port disposed on an upper end of the lower vertical portion, the access port having a lid removably disposed thereon; and an arcuate shield portion adapted for removable securement to the air flow tube, the shield portion including a central recess dimensioned for receiving the air flow tube therein, the central recess having a receiving sleeve extending inwardly therefrom for mating with a cylindrical pin extending outwardly from the air flow tube.

2. A tracheotomy tube water blocking system for preventing water from entering a trachea tube while showering comprising, in combination:

a strap adapted for securement around a neck of a wearer, the strap having an aperture through a front portion thereof, the aperture having a cylindrical collar secured therein, the cylindrical collar having an open inner end and an open outer end, the open inner end dimensioned for coupling with an existing tracheotomy tube of the wearer;

an air flow tube having a generally inverted L-shaped configuration, the air flow tube having an upper horizontal portion with an open inner end coupling with the open outer end of the cylindrical collar, the air flow tube including a lower vertical portion extending downwardly from the upper horizontal portion, the lower vertical portion having an open lower end;

and further including a cover member having a generally frustoconical configuration, the cover member having a wide inner end and a narrow outer end, the wide inner end positionable over the cylindrical collar and the narrow outer end receiving the upper horizontal portion of the air flow tube therethrough for mating with the cylindrical collar.

3. The tracheotomy tube water blocking system as set forth in claim 2 wherein the open inner end of the cylindrical collar is positioned inwardly of the strap and the open outer end is positioned outwardly of the strap.

4. The tracheotomy tube water blocking system as set forth in claim 2 wherein the cylindrical collar has an air screen disposed therein.

5. The tracheotomy tube water blocking system as set forth in claim 2 wherein the air flow tube includes an access port disposed on an upper end of the lower vertical portion, the access port has a lid removably disposed thereon.

6. The tracheotomy tube water blocking system as set forth in claim 2 and further including an arcuate shield portion adapted for removable securement to the air flow tube.

7. The tracheotomy tube water blocking system as set forth in claim 6 wherein the shield portion includes a central recess dimensioned for receiving the air flow tube therein.

8. The tracheotomy tube water blocking system as set forth in claim 7 wherein the central recess has a receiving sleeve extending inwardly therefrom for mating with a cylindrical pin extending outwardly from the air flow tube.

* * * * *